United States Patent [19]

Riecken

[11] Patent Number: 5,358,394
[45] Date of Patent: Oct. 25, 1994

[54] APPARATUS FOR MAKING AN INSOLE

[76] Inventor: George C. Riecken, 2154 Adams Ave., Evansville, Ind. 47714

[21] Appl. No.: 107,297

[22] Filed: Aug. 16, 1993

Related U.S. Application Data

[62] Division of Ser. No. 780,036, Oct. 21, 1991, Pat. No. 5,275,775.

[51] Int. Cl.$^5$ .................... A43B 10/00; A43B 19/00
[52] U.S. Cl. ........................... 425/2; 249/55; 264/223; 264/DIG. 30; 425/450.1; 425/542
[58] Field of Search ................. 425/2, 542, 450.1; 264/222, 223, DIG. 30; 249/55

[56] References Cited

U.S. PATENT DOCUMENTS

| | | | |
|---|---|---|---|
| 384,448 | 6/1888 | Keller | 425/2 |
| 486,607 | 11/1892 | Willey | 264/223 |
| 1,044,171 | 11/1912 | Guilford | 264/223 |
| 1,824,835 | 9/1931 | Pierce | 249/55 |
| 1,856,394 | 5/1932 | Lettermann | 264/223 |
| 2,136,815 | 11/1938 | Förster et al. | 12/142 N |
| 2,333,481 | 11/1943 | Limmer | 264/DIG. 30 |
| 2,742,657 | 4/1956 | Sloane | 12/142 N |
| 2,924,849 | 2/1960 | Buchman | 425/2 |
| 2,955,326 | 10/1960 | Murray | 56/324 |
| 2,961,714 | 11/1960 | Murray | 264/223 |
| 2,973,529 | 3/1961 | Silverman | 12/142 N |
| 3,262,142 | 7/1966 | Keder | 12/146 L |
| 3,504,079 | 3/1970 | Hall | 264/225 |
| 3,720,971 | 3/1973 | Wyness et al. | 12/146 C |
| 3,769,392 | 10/1973 | Tessaro | 264/46.5 |
| 3,855,657 | 12/1974 | Mazzotta | 12/142 RS |
| 3,896,202 | 7/1975 | Palau | 264/154 |
| 3,981,037 | 9/1976 | McCroskey, Sr. | 12/146 S |
| 3,983,204 | 9/1976 | Opinsky et al. | 264/244 |
| 3,985,853 | 10/1976 | Weisberg | 264/250 |
| 3,995,002 | 11/1976 | Brown | 264/571 |
| 4,139,337 | 2/1979 | David et al. | 425/2 |
| 4,470,782 | 9/1984 | Zimmerman, Jr. et al. | 425/2 |
| 4,503,576 | 3/1985 | Brown | 12/146 M |
| 4,548,563 | 10/1985 | Aigrefeuille | 425/2 |
| 4,669,142 | 6/1987 | Meyer | 12/142 N |
| 4,747,989 | 5/1988 | Peterson | 264/223 |
| 4,888,841 | 12/1989 | Cumberland | 12/38 |
| 4,906,425 | 3/1990 | Poussou | 264/102 |
| 4,932,852 | 6/1990 | Suzuki | 425/2 |
| 4,962,762 | 10/1990 | Beekil | 36/154 |
| 4,979,252 | 12/1990 | Daley | 12/142 N |
| 5,042,100 | 8/1991 | Bar et al. | 12/142 N |

FOREIGN PATENT DOCUMENTS 2721443 11/1978 Fed. Rep. of Germany.

OTHER PUBLICATIONS

"Freedom TM Foot System", AliMed ® inc. six pages, date unknown.

Primary Examiner—Jay H. Woo
Assistant Examiner—Duane S. Smith
Attorney, Agent, or Firm—Barnes & Thornburg

[57] ABSTRACT

An insert forming apparatus is provided for making an insert to conformingly fit a shoe and a person's foot within the shoe. The apparatus includes an upper and lower shell half which, when fastened together, form a foot receiving cavity that conformingly fits the individual contours of the last from which the person's shoes are made. The apparatus also includes an injection tube for injecting insert forming material into the foot receiving cavity under and about the person's foot.

4 Claims, 6 Drawing Sheets

APPARATUS FOR MAKING AN INSOLE

This is a division of application Ser. No. 07/780,036 filed Oct. 21, 1991 and granted on Jan 4, 1994 with U.S. Pat. No. 5,275,775.

BACKGROUND AND SUMMARY OF THE INVENTION

This invention relates to orthotics and specifically to orthotics that fit a foot and a shoe. The invention particularly relates to orthotics formed in a casting shell that conforms to the contours of the last of the patient's shoe.

Orthotics are known in the prior art. See for example, Meyer, U.S. Pat. No. 4,669,142; Sloane, U.S. Pat. No. 2,742,657; Daley, U.S. Pat. No. 4,979,252; and Cumberland, U.S. Pat. No. 4,888,841.

Although ready-made and custom-made orthotics have been known in the prior art there are two outstanding obstacles that interfere with the success of these products. First, there is the problem in matching the orthosis to the contour of the insole of the shoe it is to be worn in, as well as the foot's plantar surface. This is particularly the case when an orthotic technician is making soft or flexible orthotics. This takes considerable skill and some art work. If these two surfaces fail to mate perfectly the orthosis will distort under body weight and take the shape of the shoe, thus losing accommodation.

Another major problem is the fact that the foot does not always fall into the range of standard shoe sizes, widths, and last shapes, and even with a custom-made orthosis to fit a foot, the orthosis may not fit the shoe. This will mean that the orthosis may help with symptoms but may not address the cause of the problem.

The present invention makes it possible to accommodate many people in ready-made shoes who now must have their shoes custom-made. This will greatly increase their shoe style selection and reduce their costs. Additionally, there are thousands of people who badly need custom-made shoes but cannot afford them and have suffered greatly as a result. With this invention, many of them will be able to be fitted comfortably in ready-made shoes.

According to the present invention a casting shell for making an orthosis to conformingly fit a shoe and a patient's foot within the shoe comprises a shell piece which conforms to a portion of a last of the shoe, the shell piece having an opening to allow removal from the patient's foot, a mating shell piece which conforms to the rest of the last of the shoe, means for injecting an insole forming material into said shell, and means for fastening the shell pieces together about a foot.

In a preferred embodiment of the present invention a casting shell is provided for making an insole to conformingly fit a shoe and a patient's foot within the shoe. The casting shell comprises an upper shell half which conforms to a last of the shoe, the upper shell half having an opening flange to allow removal from the patient's foot, a lower shell half which conforms to the last of the shoe and has an aperture in the medial arch area, an injector tube coupled to the aperture in the lower shell half for injecting insole forming material, fasteners for fastening the upper and lower shell halves together, and a clamp for maintaining the opening flange in the closed position while injecting insole forming material.

The present invention also comprises a method for making an insole to conformingly fit a shoe and a patient's foot within the shoe. The method comprises the steps of obtaining an appropriate sized shoe having a deep last to provide room to accommodate the insole and the foot, obtaining a shell made from the last from which the shoe is made, placing the patient's foot in the shell, injecting a curable insole forming material under and about the patient's foot to fit the contour of the foot and the interior of the shell, curing the insole forming material, and removing the insole and placing it in the shoe.

In a preferred embodiment of the invention, the shell has an upper shell half and a lower shell half joined together at a parting line about generally the largest perimeter of the shell and means for fastening the upper and lower shell halves together. Insole forming material is then injected into the lower shell half under and about the patient's foot to form a shape that fits the patient's foot and the shell.

To practice the invention, spacing tape may be affixed to the bottom sides of the last from which the patient's shoe is made. The spacing tape should have a thickness that is substantially equal to that of the lower shell half material. The last is then inverted in a sand casting box and a suitable casting material such as Liquid Last, a product of Riecken's Orthotic Laboratory, which material is made from talc, polyester resin, and microcellular glass beads or plaster, is poured over the last to form a mold. The mold should have the proper heel height for the last cast into it. The edges of the mold should turn up around the sides of the last to the last's widest perimeter leaving a ledge along the edge of the last for the upper half of the casting shell to mate with.

This mold of Liquid Last can be used as the lower shell half, however it is an opaque, heavy, and solid block of expensive material. Thus, for production purposes it may be modified slightly and used as a master mold for forming the production casting shells on a vacuum forming machine. The mold is removed, trimmed as appropriate, and holes are drilled through the mold to communicate a vacuum from the vacuum forming machine to the material to be vacuum formed. A heated blank of lower shell half material is placed over the mold on the vacuum forming machine and drawn down by the vacuum forming machine. That lower shell half is then removed from the mold and a second blank of lower shell half material is drawn down to form a second lower shell half. One of those lower shell halves is put aside for use as the lower portion of a casting shell, and the other lower shell half has holes drilled through it to coincide and align with the holes previously drilled in the mold. These holes are drilled to allow the vacuum to communicate between the vacuum forming machine and the upper shell half material to be formed by the vacuum forming machine. The second lower shell half is then reinserted in the mold and the last is placed therein. A notch is cut through the lower shell half and into the mold at a position adjacent to the heel curve of the last. A flange forming piece is then mounted on the last and the last is inserted into the foot receiving cavity of the lower shell half ensuring that the flange forming piece engages the notch in the lower shell half and the mold. A blank of upper shell half material is then drawn down over the last and the lower shell half. The upper shell half is removed and trimmed to provide a hole for the ankle and to allow the upper shell half opening flange to open and close. The upper shell half is laid on and aligned with the lower shell half and fastener receiving holes are drilled through mating flanges formed in the shell halves. Injector tube holes are drilled in the medial arch area to accommodate a filler tube for injecting the insole forming materials.

In one preferred embodiment of the invention, an insole cover is placed in the foot receiving cavity of the lower shell half, the patient's foot is placed on the insole cover, and the position of the fastener receiving holes are marked on the insole cover. The insole cover is removed, the holes are punched through, and the insole cover is replaced in the foot receiving cavity. The patient's foot is lightly placed on top of the insole cover and the insole cover is then adjusted to align the holes punched therein to align with the fastener receiving holes. The upper shell half is then placed over the patient's foot and fasteners are inserted through the fastener receiving holes, thereby joining the upper shell half, the lower shell half, and holding the insole cover therebetween. Insole forming material is then injected through the injection tube into the lower shell half under and about the patient's foot.

The present invention can be practiced for various purposes. One such use is as a sizing device. The clear plastic casting shell base alone lets you see at a glance, once a foot is placed in it, if the size is proper. These bases would be of great assistance as fitting devices in all shoe stores, even self-service stores. A second use would be to improve fit and comfort of ready-made footwear to the extent that in many cases ready-made footwear can be made as comfortable as custom-made footwear. By sizing patients in casting shells, in accordance with the invention, a technician can determine the true insole size needed for comfort and proper function and can form insoles that will be the exact shape of feet and thick enough to take up any excess room in ready-made shoes.

A third use of the casting shells would be to serve as a mold to cast, fabricate, or heat form custom orthosis for the foot's plantar surface area. After the proper size shell has been selected, it is used as a form in which to assemble needed modalities on a full or partial insole to make a custom orthotic.

Another and important use of the casting shell is to accommodate partial amputations and/or mis-mated foot conditions. When dealing with major amputations, the bottom of the orthosis can be made up in the casting shell out of fiberglass. This gives the rigidity needed to prevent the shoe from folding back and it also becomes a spring that stores energy from the gait cycle to aid in toe off situations. If the amputation has been rather extensive, such as a chopart, lisfranc, or transmetatarsal, a filler block of flexible foam may be formed. It can be made of urethane or silicone foam and can be formed in the casting shell so as to become part of the orthotic. It preferably should not extend closer than one-half inch to the anterior end of the foot, this remaining space being filled with accommodative visco elastic polymer. This saves considerable weight, eliminates the need for a high, rigid rocker and improves function.

Additional objects, features, and advantages of the invention will become apparent to those skilled in the art upon consideration of the following detailed description of preferred embodiments exemplifying the best mode of carrying out the invention as presently perceived.

DETAILED DESCRIPTION OF THE DRAWINGS

Figure 1:
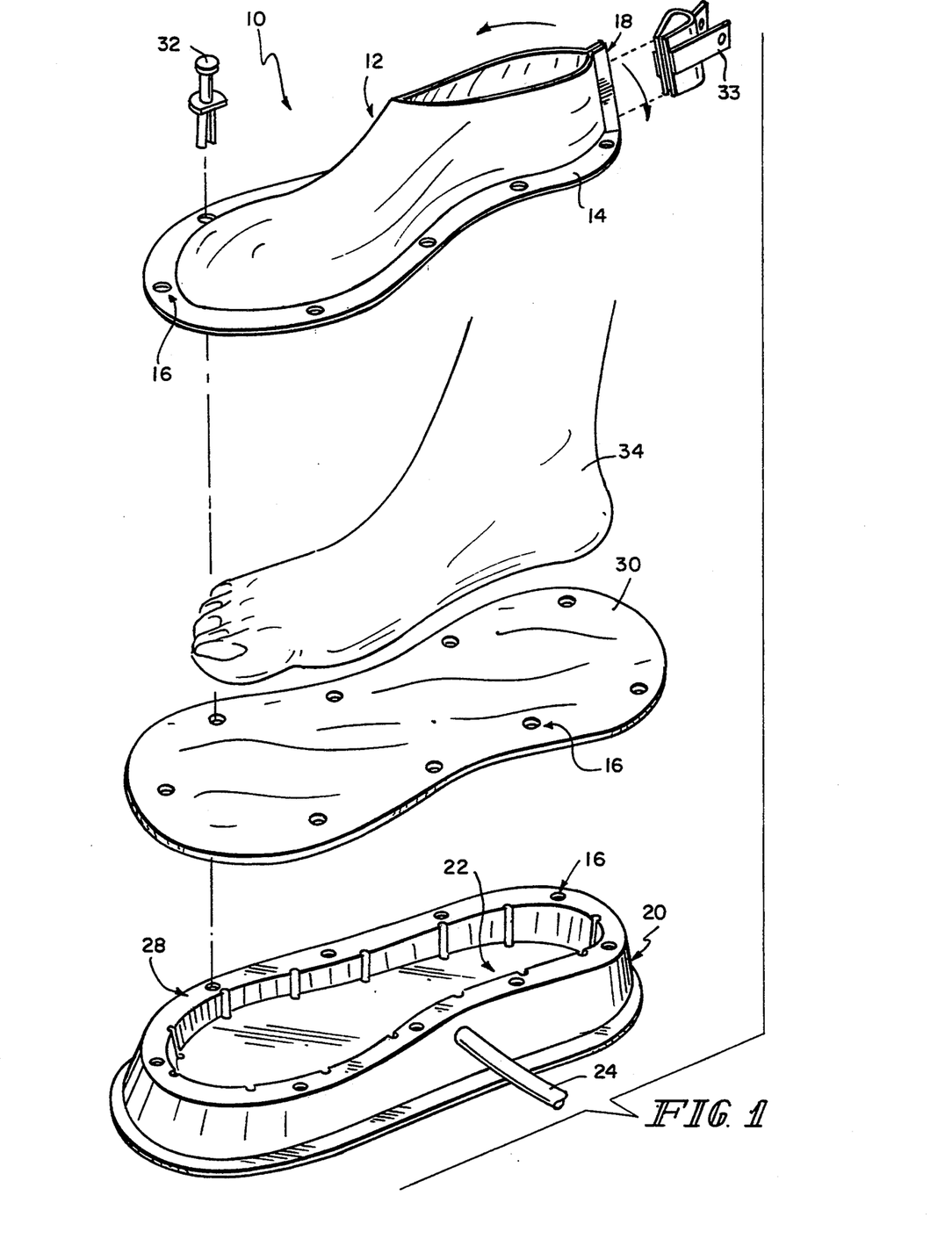
FIG. 1 is an exploded view of the upper and lower shell halves.

A preferred embodiment of the orthotic forming casting shell 10 shown in FIG. 1 comprises an upper shell half 12 formed to include a lower flange 14 having a plurality of fastener receiving holes 16, the shell half 12 being formed to include an upper shell opening flange 18. The casting shell 10 also includes a first lower shell half 20 formed to include a foot receiving cavity 22, the cavity being joined to an injection tube 24 and being in communication with an injection source 26. The first lower shell half 20 is also formed to include an upper flange 28 having a plurality of fastener receiving holes 16. When the upper flange 28 and the lower flange 14 are in registry with an insole cover 30 having a plurality of fastener receiving holes 16 positioned therebetween, the fastener receiving holes 16 of the upper flange, lower flange and insole cover are in alignment. Then, fasteners 32 may be inserted through the aligned openings for holding the upper shell half 12, the first lower shell half 20 and the insole cover 30 in fixed position relative to each other. A clamp 33 is provided to hold the upper shell opening flange 18 in the closed position and removed to allow entry of a foot 34 into the foot receiving cavity 22.

Figure 2:
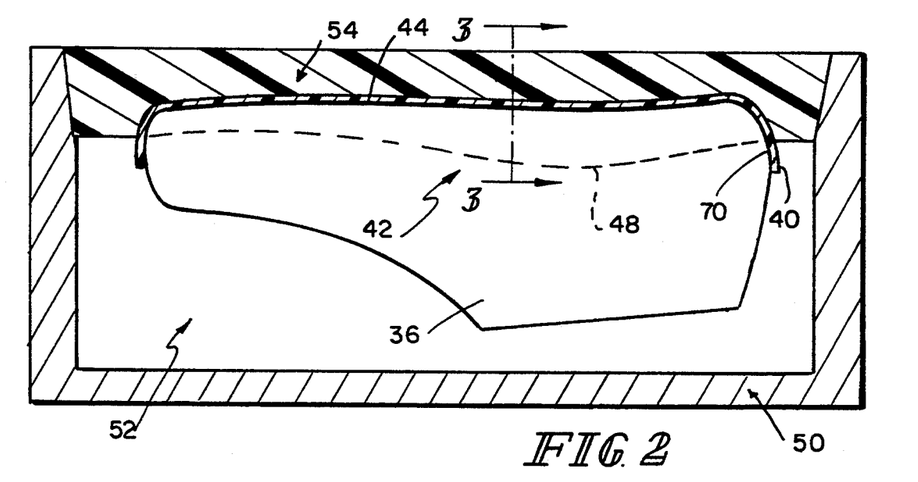
FIG. 2 is a sectional view of a casting box with a shoe last positioned therein, and a mold of the bottom portion of the last.

In practicing the method of this invention, a last 36 from which the patient's shoe 38 is made is obtained. Preferably, spacing tape 40 is affixed to the sides 42 and bottom 44 of the last 36, the thickness of the spacing tape 40 closely approximating the thickness of the lower shell half material 46. The line of widest perimeter 48 is marked on the spacing tape 40, the last 36 is inverted and placed in a casting box 50, and sand 52, or other suitable material, is packed around the last 36 up to the line of widest perimeter 48. The last should be positioned in the casting box to provide for the proper heel height of the last. Liquid Last, plaster of paris, or other suitable mold material is then used to fill the remainder of the casting box 50 and allowed to cure, forming a mold 54 of the lower portion of last 36 with allowance for the lower shell half thickness and the proper heel height.

Figure 3:
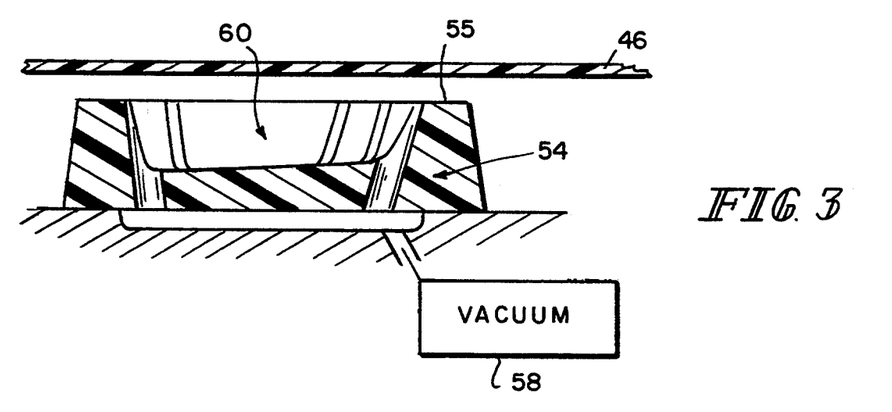
FIG. 3 is a sectional view taken along lines 3—3 in FIG. 2 of the mold with the mold inverted and positioned on a vacuum chamber and having holes drilled through the mold to communicate the vacuum to a lower shell half to be vacuum formed on the mold.
Figure 4:
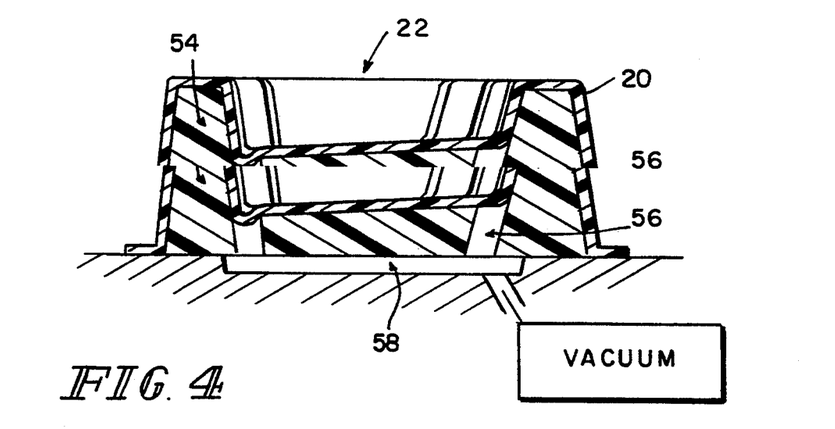
FIG. 4 is a sectional view of the mold with a first lower shell half vacuum formed on the mold.
Figure 5:
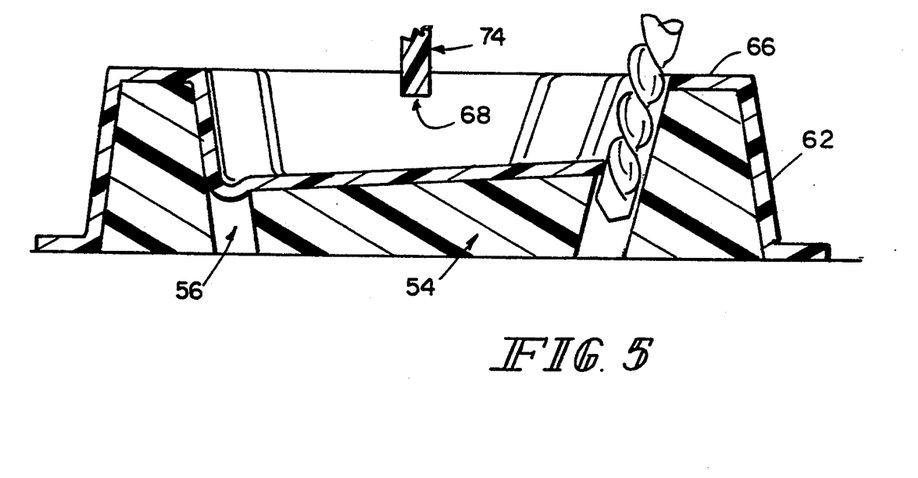
FIG. 5 is a sectional view showing a second lower shell half formed on the mold with holes being drilled therethrough to communicate the vacuum from the vacuum chamber through the second lower shell half.
Figure 6:
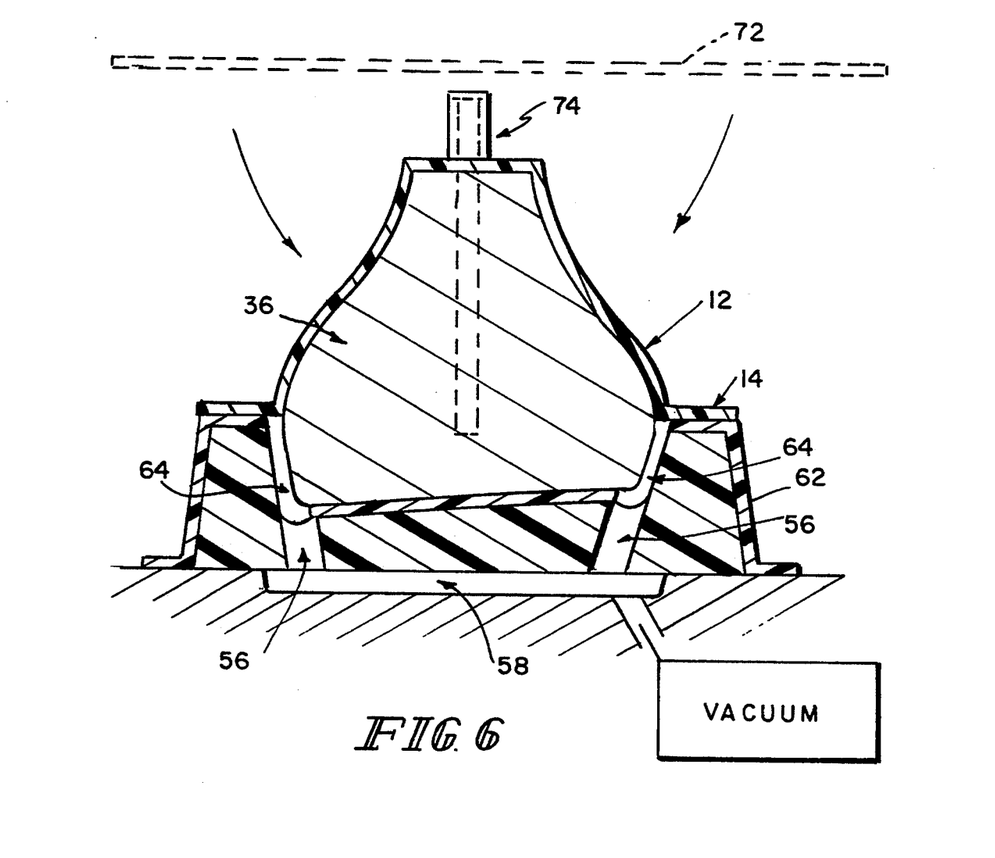
FIG. 6 is a sectional view of the last positioned in the second lower shell half and mold, the vacuum communication holes, and the upper shell half vacuum formed onto the last and the second lower shell half.
Figure 7:
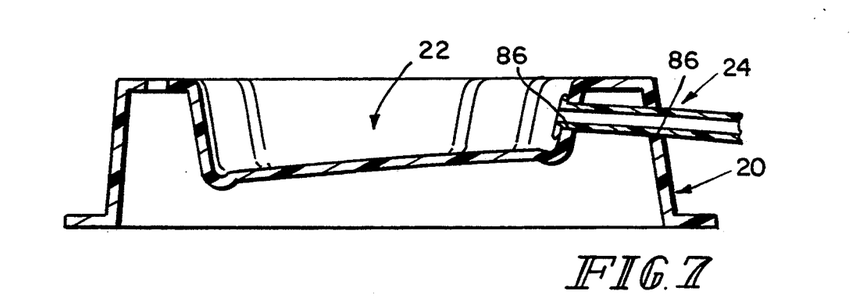
FIG. 7 is a sectional view of the first lower shell half out of the mold, with an injection tube joined thereto for injecting insole forming material.

The mold 54 as just formed would be suitable for use with the upper shell half 12 to practice the invention. However, since the mold material is opaque, heavy, and expensive, a preferred embodiment of the invention uses a transparent shell made using the mold in the following manner. After curing, the mold 54 is removed and shaped to include an upper flange forming ledge 55, and holes 56 are drilled through the mold 54 to form a vacuum passageway between a vacuum chamber 58 and the imprint cavity 60 of the last 36 in the mold 54, with the vacuum passageway extending along the sides of the imprint cavity 60 to include a portion of the upper flange forming ledge 55. A sheet of thin transparent material 46, such as General Electric's Lexan, which material is a polycarbonate, or a high density polyethylene about 0.060 inches thick, is then drawn down over the mold 54 using standard vacuum forming techniques, as shown in FIGS. 3 and 4, forming a first lower shell half 20. The first lower shell half 20 is removed, and a second lower shell half 62 is formed using standard vacuum forming techniques. Vacuum holes 64 are drilled into the second lower shell half 62 to align with, and act as a continuation of, the mold vacuum holes 56 to extend the vacuum passageway to the mating surface 66 of the upper flange 28. A notch 68 is cut through the second lower shell half 62 and into the mold 54 in line with the heel curve 70 of the last 36. With the exception of the notch 68 and vacuum holes 64, the second lower shell half 62 is substantially identical to the first lower shell half 20, and the uses for either can be reversed.

With the second lower shell half 62 in the mold 54, the last 36 is placed in the second lower shell half 62. A flange forming piece 74 is mounted on the last 36 to extend along the heel curve 70 from the top of the last 36 to the bottom of the notch 68 in the mold 54, passing through the second lower shell half 62. A blank of upper shell half material 72 with more flexibility than the lower shell half material 46, such as 0.060 inch thick low density polyethylene, is drawn down over the last 36 and the second lower shell half 62 and around the flange forming piece 74 using standard vacuum forming techniques. Due to shrinkage of the low density polyethylene during curing, a suitable spacing pad may be affixed to the toe of the last. The upper shell half 62 is removed and trimmed to provide for an opening in the top for an ankle and any excess material on the upper shell opening flange 18 is removed to allow the opening flange 18 to open to allow entry of a foot into the foot receiving cavity 22. The upper shell half 12 is aligned with the first lower shell half 20 so that the upper flange 28 and the lower flange 14 are in registry, and fastener receiving holes are drilled through both flanges 28, 14. Injection tube holes 86 are drilled through the first lower shell half 20 and an injection tube 24 is fitted therethrough, as shown in FIGS. 7–11. Thus, the shell obtained matches the interior of the desired shoe and comprises at least two shell parts which, when held together, form the casting shell 10.

Of course, the shell could also be obtained by forming a thin plastic shell about the last to correspond to the interior of the shoe. The resulting plastic shell could then be divided into at least two parts so that the shell can receive the foot.

Figure 8:
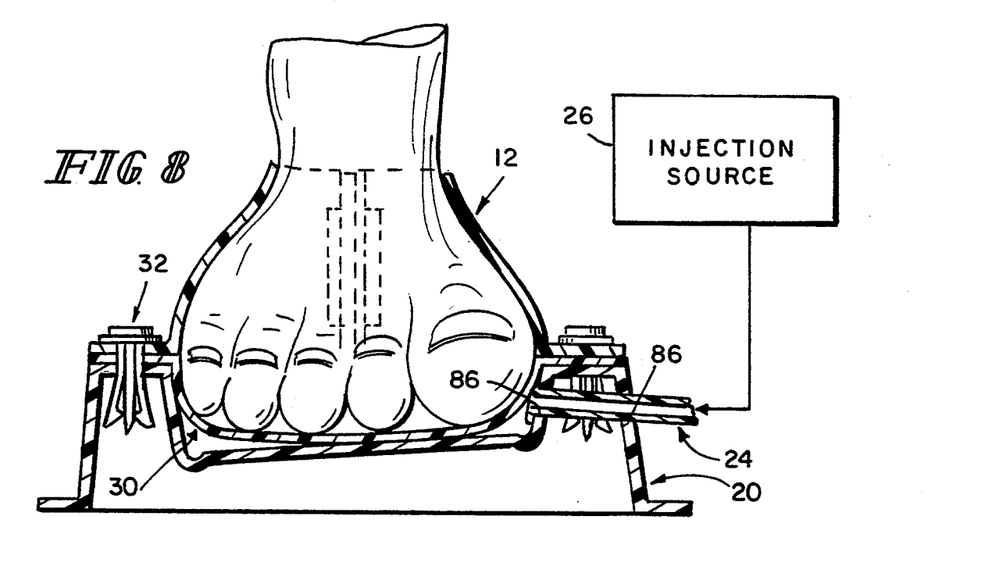
FIG. 8 is a sectional view of the first lower shell half, the upper shell half, an insole cover fastened therebetween, and the injection tube.
Figure 9:
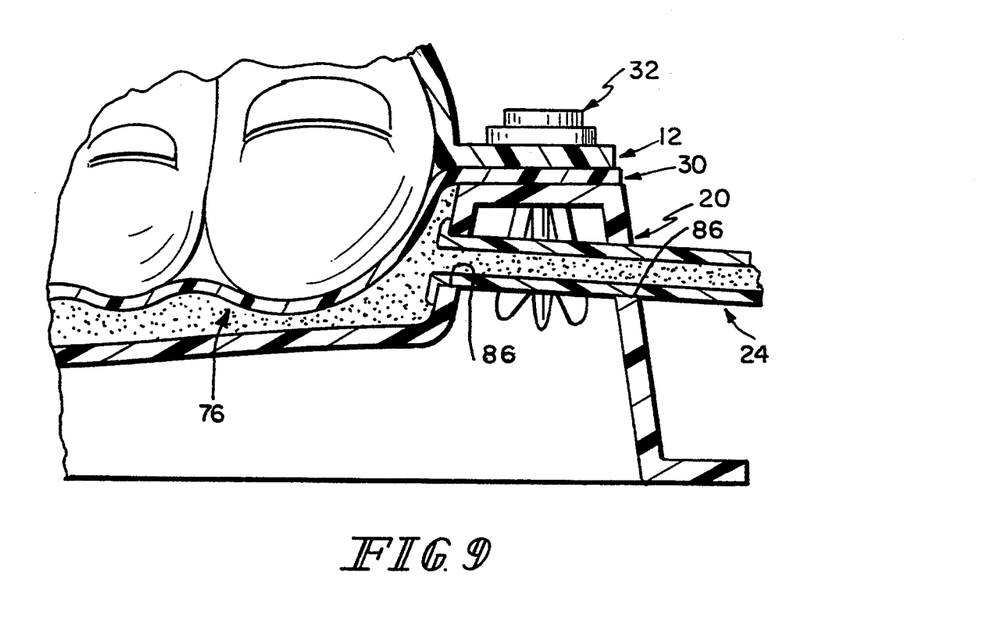
FIG. 9 is an enlarged fragmentary view of the FIG. 8 section showing the insole forming material, the first lower shell half and the insole cover.

FIG. 8 shows the embodiment of FIG. 1 ready for the injection of insole forming material 76, and FIG. 9 shows the insole forming material 76 in place under and about the patient's foot.

Figure 10:
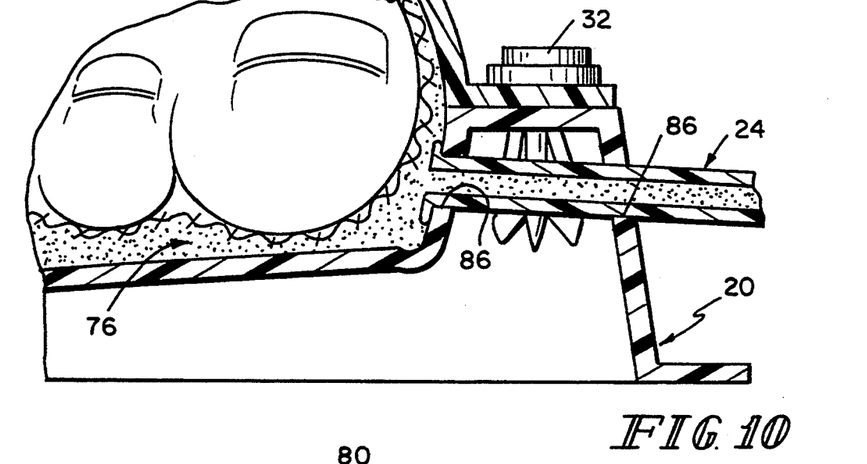
FIG. 10 shows an alternative embodiment wherein a patient wears a sock during the injection process.

FIG. 10 shows an alternative embodiment of the invention showing a patient wearing a sock during the injection of the insole forming material 76 in lieu of using an insole cover 30 or casting balloon 80.

Figure 11:
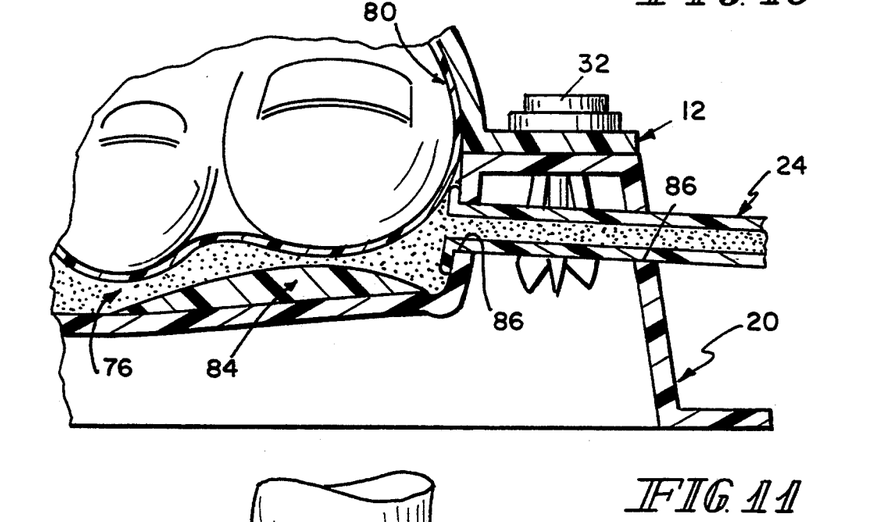
FIG. 11 shows an alternative embodiment wherein the patient wears a casting balloon to avoid skin contact with the insole forming material, and modalities are placed in the first lower shell half to become part of the orthotic.

FIG. 11 depicts another alternative embodiment where a modality 84 is placed in the foot receiving cavity 22 and molded into the orthotic with the insole forming material 76. Also depicted is a casting balloon 80 on the patient's foot 34.

Figure 12:
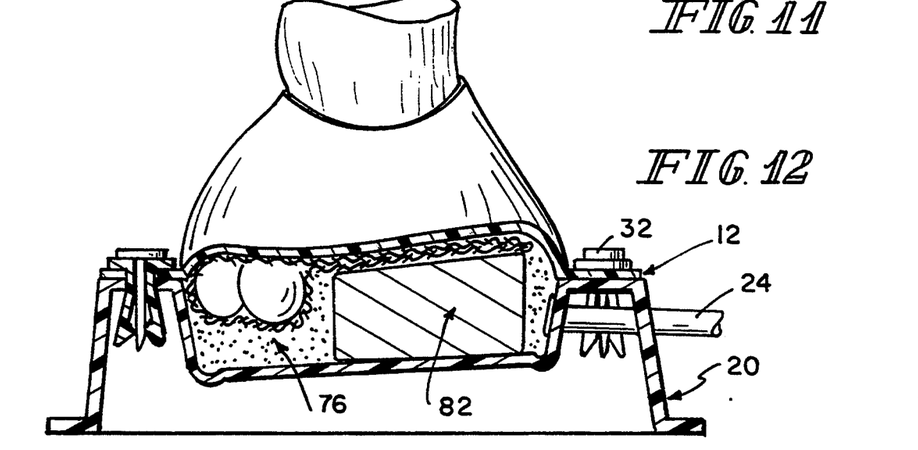
FIG. 12 is an alternative embodiment in the case of a patient with a partial amputation, the figure showing the addition of a second, dissimilar material to be joined to the insole forming material to form the orthotic.
Figure 13:
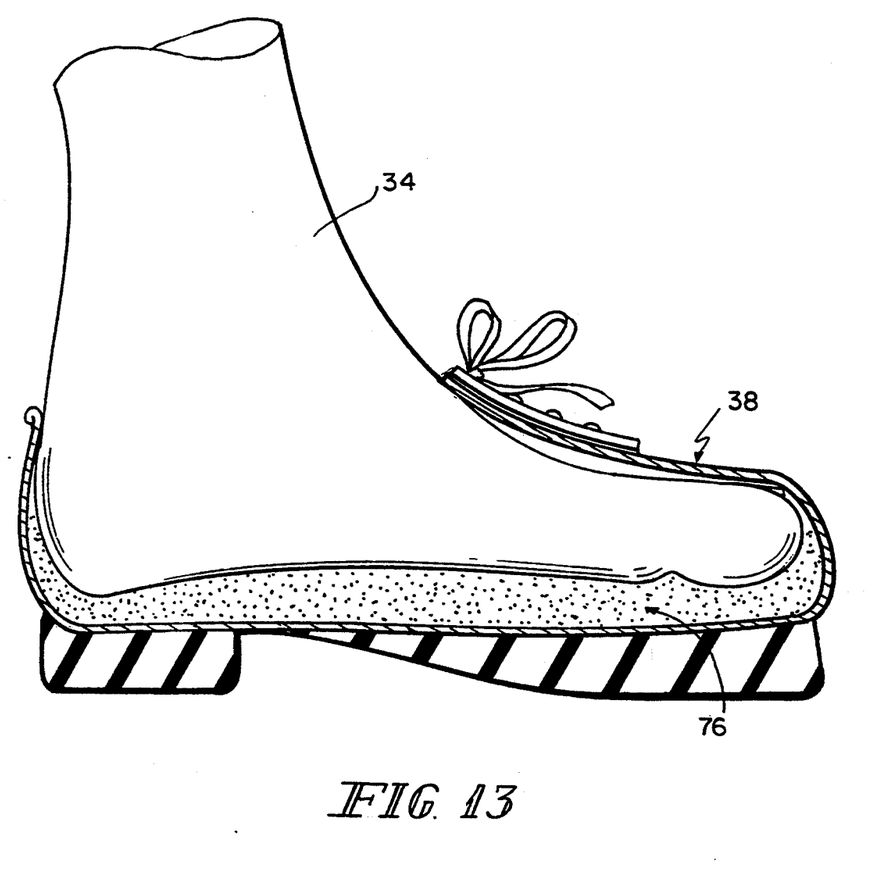
FIG. 13 is a sectional view of a patient wearing an orthosis that conformingly fits the foot and the shoe.

FIG. 12 is yet another embodiment in the case of a partial amputation. A filler block 82 of flexible foam can be formed in the casting shell. It should not extend closer than one-half inch to the anterior end of the foot. This remaining space would be filled with a accommodative visco elastic polymer saving weight and eliminating the need for a high, rigid rocker, and improves function. The bottom of the orthotic can be made out of fiberglass if required to provide rigidity needed to prevent the shoe from folding back and provide a spring that stores energy from the gait cycle to aid in toe off.

Although the invention has been described in detail with reference to certain preferred embodiments, variations and modifications exist within the scope and spirit of the invention as described and defined in the following claims.

What is claimed is:

1. A casting shell for making an insole to conformingly fit a shoe and a patient's foot within the shoe comprising
    an upper shell half having a shape which conforms to a last of the shoe, the upper shell half having an opening flange to allow removal from the patient's foot,
    a lower shell half having a shape which conforms to the last of the shoe and has an aperture in the medial arch area,
    an injector tube coupled to the aperture in the lower shell half for injecting insole forming material,
    fasteners for fastening the upper and lower shell halves together, and
    a clamp for maintaining the opening flange in the closed position while injecting insole forming material.

2. A casting shell for making an orthosis to conformingly fit a shoe and a patient's foot within the shoe comprising
    a shell piece having a shape which conforms to a portion of a last of the shoe, the shell piece having an opening to allow removal from the patient's foot, a mating shell piece having a shape which conforms to the rest of the last of the shoe, means for injecting an insole forming material into said shell, and means for fastening the shell pieces together about a foot.

3. An apparatus for making an insert to conformingly fit a shoe and a patient's foot within the shoe comprising a casting shell having a shape which conforms to a last of the shoe, wherein the casting shell includes an upper shell half having a shape which conforms to the upper portion of a last of the shoe, and a lower shell half having a shape which conforms to the lower portion of the last of the shoe, and means for injecting insert forming material into the casting shell.

4. The apparatus of claim 3 wherein the lower shell is formed to include an aperture and the means for injecting includes an injector tube coupled to the aperture in the lower shell half.

* * * * *